US00PP37032P3

(12) United States Plant Patent
Sawamura et al.

(10) Patent No.: US PP37,032 P3
(45) Date of Patent: Oct. 21, 2025

(54) APPLE TREE NAMED 'BENITSURUGI'

(50) Latin Name: ***Malus domestica* (Suclow) Borkh**
Varietal Denomination: BENITSURUGI

(71) Applicant: NATIONAL AGRICULTURE AND FOOD RESEARCH ORGANIZATION, Ibaraki (JP)

(72) Inventors: Yutaka Sawamura, Morioka (JP); Shigeki Moriya, Bunkyo-ku (JP); Kazuyuki Abe, Funagata-machi (JP); Kazuma Okada, Tsukuba (JP); Taku Shimizu, Morioka (JP); Hiroshi Iwanami, Morioka (JP); Nobuhiro Kotoda, Saga (JP); Takashi Haji, Tsukuba (JP); Sae Takahashi, Utsunomiya (JP); Yuki Moriya, Morioka (JP); Hirohisa Nesumi, Tsukuba (JP); Ayato Hori, Morioka (JP); Takashi Baba, Morioka (JP)

(73) Assignee: NATIONAL AGRICULTURE AND FOOD RESEARCH ORGANIZATION, Tsukuba (JP)

( * ) Notice: Subject to any disclaimer, the term of this patent is extended or adjusted under 35 U.S.C. 154(b) by 0 days.

(21) Appl. No.: 18/789,972

(22) Filed: Jul. 31, 2024

(65) Prior Publication Data

US 2025/0081866 P1 Mar. 6, 2025

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ... A01H 5/08; A01H 5/00; A01H 5/02; A01H 6/7418; A01H 6/74
See application file for complete search history.

(56) References Cited

U.S. PATENT DOCUMENTS

PP6,519 P * 1/1989 Yoshida ..... Plt./161

* cited by examiner

*Primary Examiner* — June Hwu
(74) *Attorney, Agent, or Firm* — Seckel IP, PLLC

(57) ABSTRACT

A new variety of apple tree 'BENITSURUGI' that has columnar tree type, bearing on spurs only, thick to very thick shoot thickness, short internode length, long leaf blade length, long petiole length, short to medium fruit stalk length, medium size and short to medium height fruit with fully open locules.

11 Drawing Sheets

Common name: Apple.

Botanical classification: *Malus domestica* (Suclow) Borkh.

Variety denomination: 'BENITSURUGI'.

CROSS-REFERENCE TO RELATED APPLICATION

This application claims priority of Japanese plant variety rights application No. 37015 filed Aug. 31, 2023, the entire content of which is incorporated by reference herein.

BACKGROUND OF THE NEW VARIETY

The present invention relates to a new and distinct variety of apple tree, *Malus domestica* (Suclow) Borkh, which has been given the variety denomination 'BENITSURUGI'.

ORIGIN OF THE VARIETY

The parent varieties are '5-12786' (male parent) (not patented) and 'SANSA' (female parent) (U.S. Plant Pat. No. 6,519), respectively.

The variety was developed and propagated at the Morioka Research Station, Institute of Fruit Tree and Tea Science, National Agriculture and Food Research Organization (NARO), in Morioka, Iwate, Japan.

The variety was reproduced asexually by vegetative reproduction by grafting one-year-old cuttings on rootstocks.

In 2005, crossing the parent varieties and collecting seeds.

In 2006, columnar type's seedlings are selected by SCAR682 DNA marker from growing seedlings.

In 2007, they were grafted on JM1 root stock.

In 2008, they were transplanted at breeding field. And selected individual plant.

In 2015, the instant plant was selected as a promising breeding line and provisionally named 'Morioka 74'.

In 2016, growing test for local adaptability were started under confidentiality conditions at 16 public testing stations in Japan.

On Aug. 31, 2023, an application for plant variety rights No. 37015 was filed for the present variety in the Japanese Plant Variety Protection Office of the Ministry of Agriculture, Forestry and Fisheries (MAFF), Japan.

Cultivation of the variety does not require special conditions or treatments.

The variety is currently mainly intended for fruit production (table use).

SUMMARY OF THE VARIETY

The present variety is distinguished by columnar tree type, bearing on spurs only, thick to very thick shoot thickness, short internode length, long leaf blade length, long petiole length, short to medium fruit stalk length, medium size and short to medium height fruit with fully open locules, that distinguish it, notably from its male parent '5-12786' (medium extent of anthocyanin overcolor of young fruit, late harvest time) and female parent 'SANSA' (ramified tree type, medium shoot thickness, medium internode length, early harvest time), as well as from reference varieties 'SENSHU' (ramified tree type, bearing on spurs and long shoots, thin to medium shoot thickness, medium internode length, medium leaf blade length, short to medium petiole length, fruit with moderately open locules) and 'SHINANO SWEET' (ramified tree type, bearing on spurs and long shoots, thin to medium shoot thickness, medium internode length, short to medium leaf blade length, short to medium petiole length, medium to long fruit stalk length, large size and tall height fruit).

A comparison with the male parent '5-12786' is as follows (evaluation based on averages):

TABLE 1

| No. | Characteristics | Male parent '5-12786' States | Present variety 'BENITSURUGI' States |
|---|---|---|---|
| 34 | Young fruit: extent of anthocyanin overcolor | medium | absent or very small to small |
| 101 | Time of harvest | late | medium |

A comparison with the female parent 'SANSA' is as follows (evaluation based on averages):

TABLE 2

| No. | Characteristics | Female parent 'SANSA' States | Present variety 'BENITSURUGI' States |
|---|---|---|---|
| 2 | Tree: type | ramified | columnar |
| 9 | One-year-old shoot: thickness | medium | thick to very thick |
| 10 | One-year-old shoot: length of internode | medium | short |
| 101 | Time of harvest | early | medium |

A comparison with the reference varieties 'SENSHU' and 'SHINANO SWEET' is as follows (evaluation based on averages):

TABLE 3

| No. | Characteristics | Reference variety 'SENSHU' States | Reference variety 'SHINANO SWEET' States | Present variety 'BENITSURUGI' States |
|---|---|---|---|---|
| 2 | Tree: type | ramified | ramified | columnar |
| 6 | Tree: type of bearing | on spurs and long shoots | on spurs and long shoots | on spurs only |
| 9 | One-year-old shoot: thickness | thin to medium | thin to medium | thick to very thick |
| 10 | One-year-old shoot: length of internode | medium | medium | short |

TABLE 3-continued

| No. | Characteristics | Reference variety 'SENSHU' States | Reference variety 'SHINANO SWEET' States | Present variety 'BENITSURUGI' States |
|---|---|---|---|---|
| 15 | Leaf blade: length | medium | short to medium | long |
| 16 | Leaf blade: width | narrow to medium | narrow to medium | medium to broad |
| 22 | Petiole: length | short to medium | short to medium | long |
| 23 | Petiole: extent of anthocyanin coloration from base | | medium | small |
| 30 | Flower: predominant color at balloon stage | | light pink | dark pink |
| 34 | Young fruit: extent of anthocyanin overcolor | large | | absent or very small to small |
| 61 | Fruit: size | | large | medium |
| 62 | Fruit: height | | tall | short to medium |
| 86 | Fruit: length of stalk | medium | medium to long | short to medium |
| 98 | Fruit: aperture of locules (in transverse section) | moderately open | | fully open |
| 101 | Time of harvest | | medium to late | medium |

BRIEF DESCRIPTION OF THE DRAWINGS

In the accompanying drawings, which are as nearly true as is reasonable possible to make in a color illustration of this type.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'BENITSURUGI' plants evaluated from 2020 to 2022 (including for the comparison with the reference plants 'SENSHU' and 'SHINANO SWEET'. The age of the plants shown on the photographs and evaluated was 8 years, 5 months on Oct. 2, 2020. Values as provided are averages.

The plants shown on the photographs were grown at Morioka, Iwate, Japan.

Figure 1:
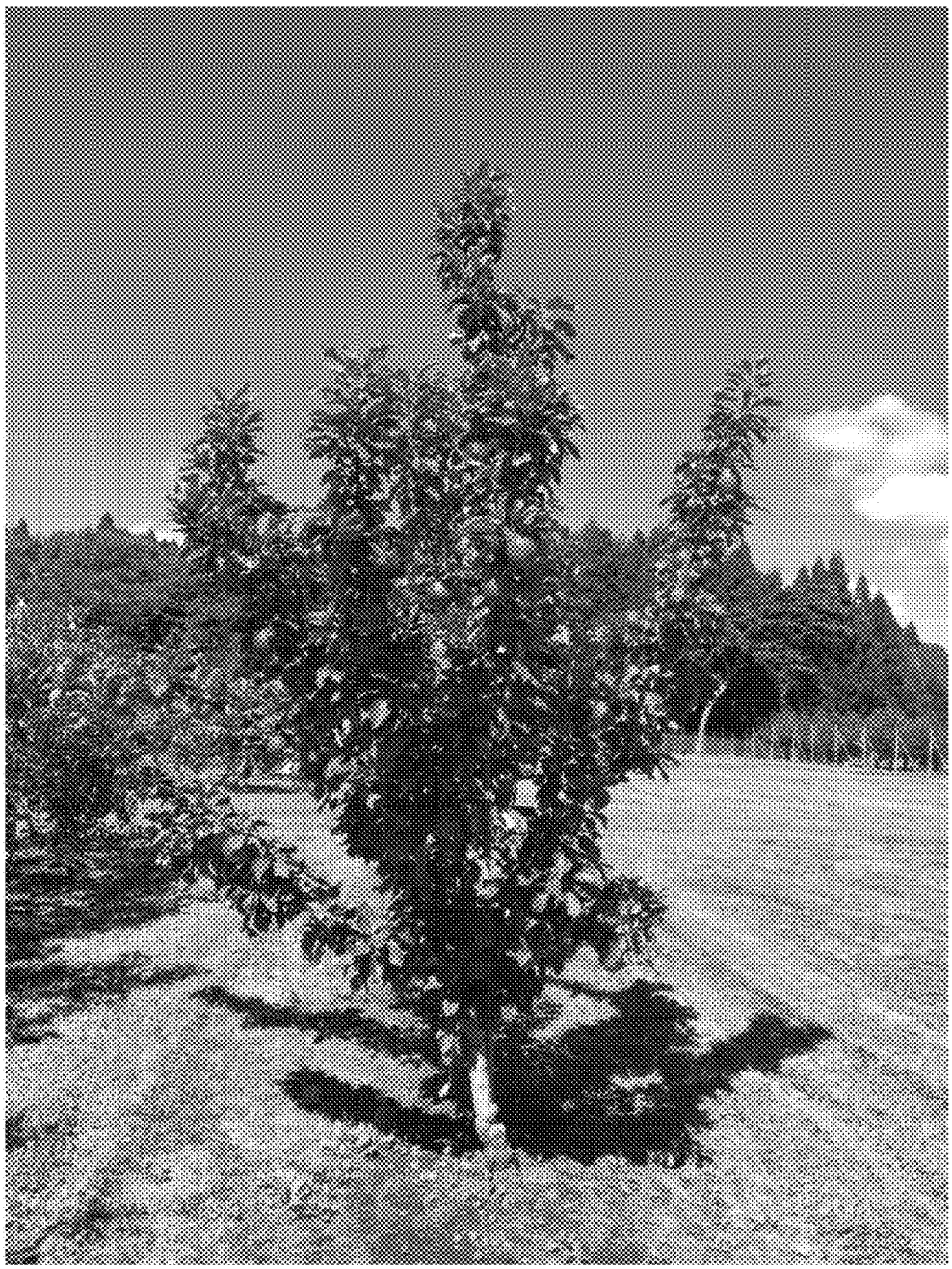
FIG. 1 is a color photograph showing a general view of the apple tree named 'BENITSURUGI' at harvest time.
Figure 2:
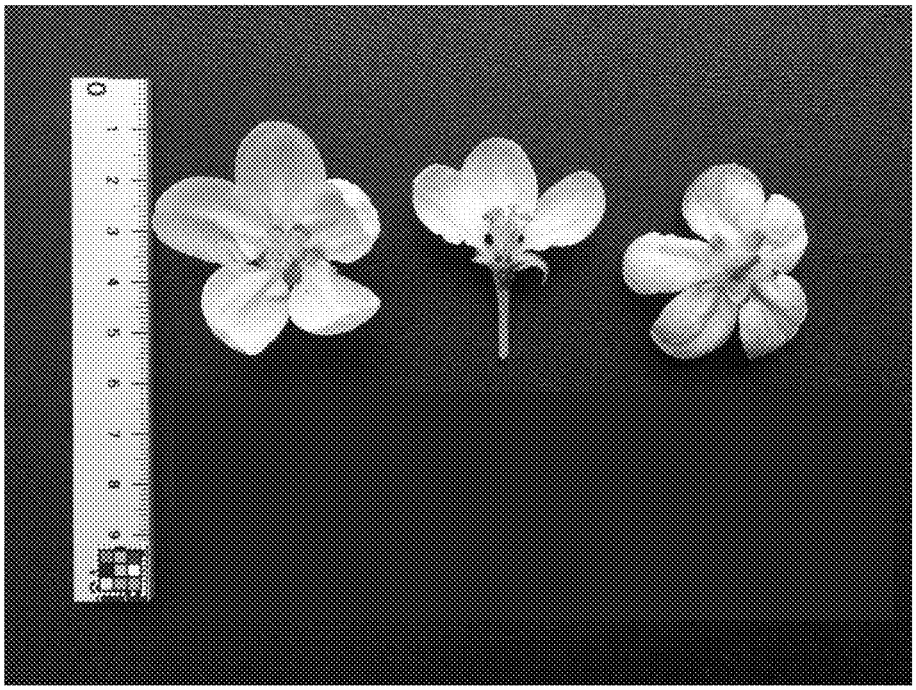
FIG. 2 is a color photograph showing a flower of 'BENITSURUGI'.
Figure 3:
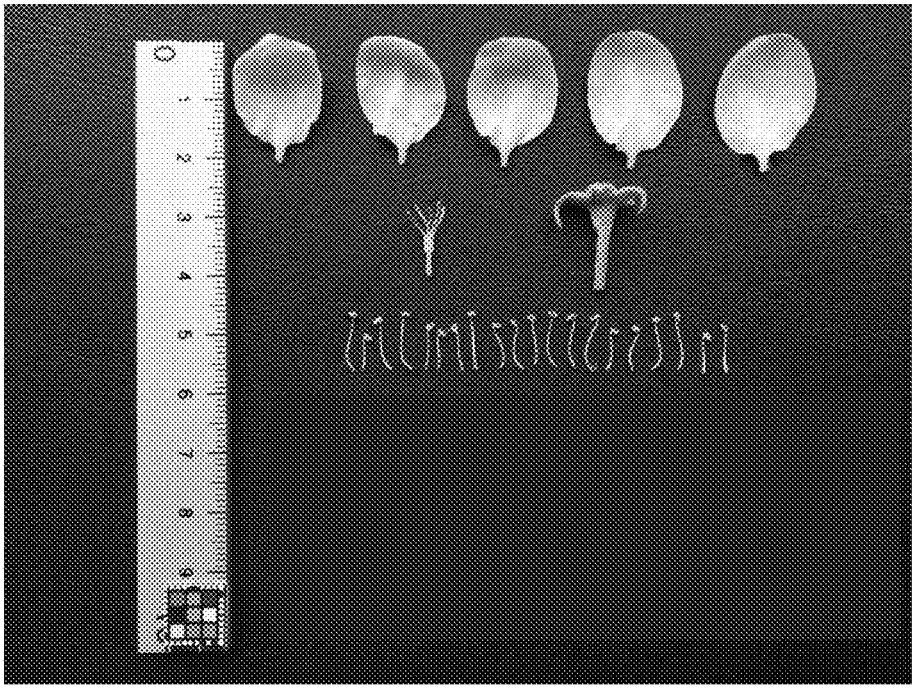
FIG. 3 is a color photograph showing detached upper surface petals, pistils, flowering stalk including calyx and detached stamens of the flower of 'BENITSURUGI'.
Figure 4:
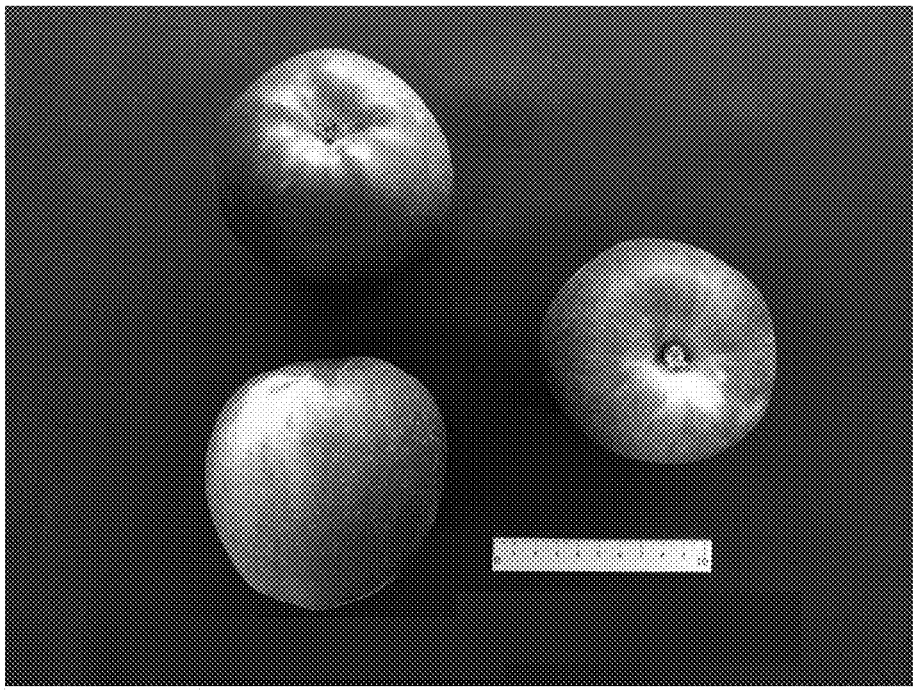
FIG. 4 is a color photograph showing fruits of 'BENITSURUGI'.
Figure 5:
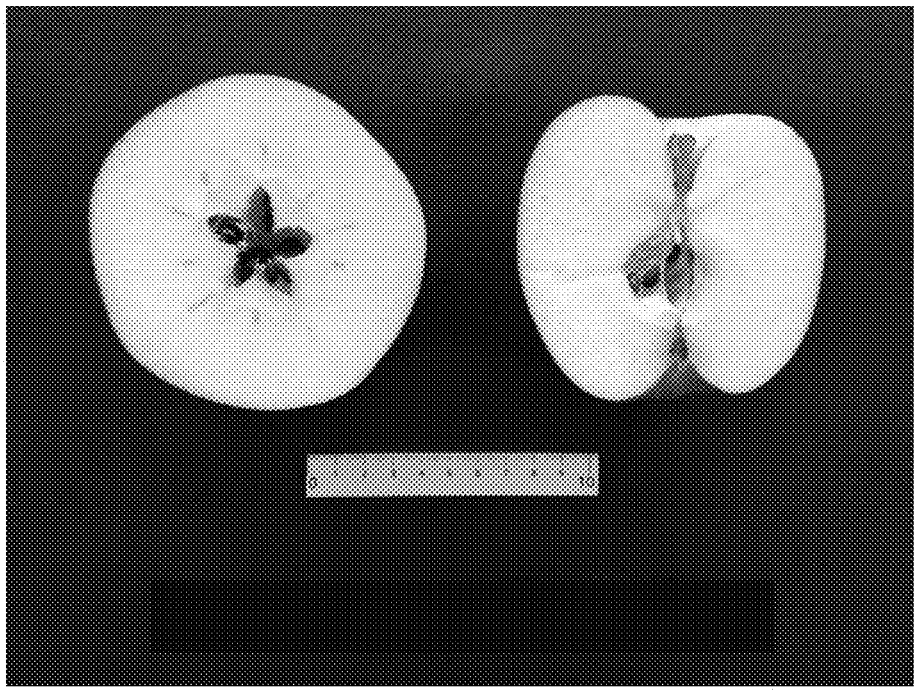
FIG. 5 is a color photograph showing cross sections of fruits of 'BENITSURUGI'.
Figure 6A:
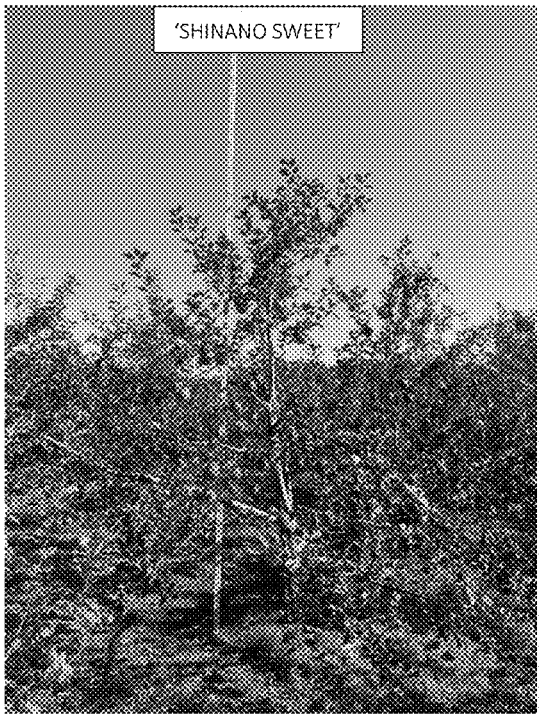
FIG. 6A is a color photograph showing the tree type of reference variety 'SHINANO SWEET'.
Figure 6B:
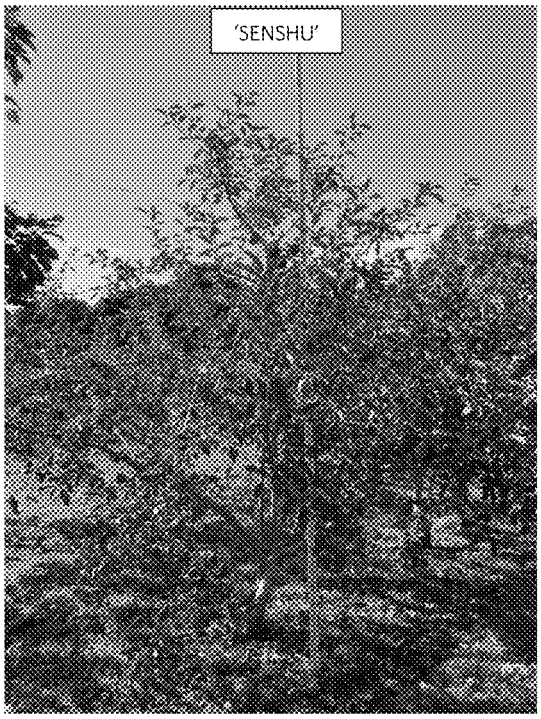
FIG. 6B is a color photograph showing the tree type of reference variety 'SENSHU'.
Figure 6C:
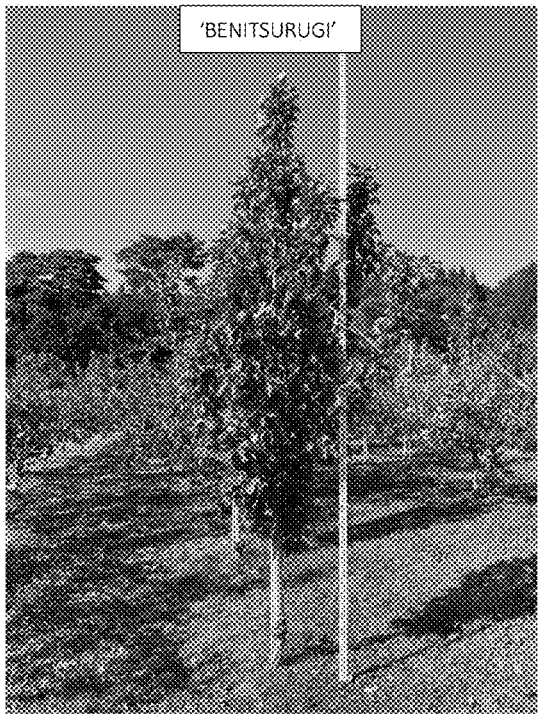
FIG. 6C is a color photograph showing the tree type of the present variety 'BENITSURUGI'.
Figure 7:
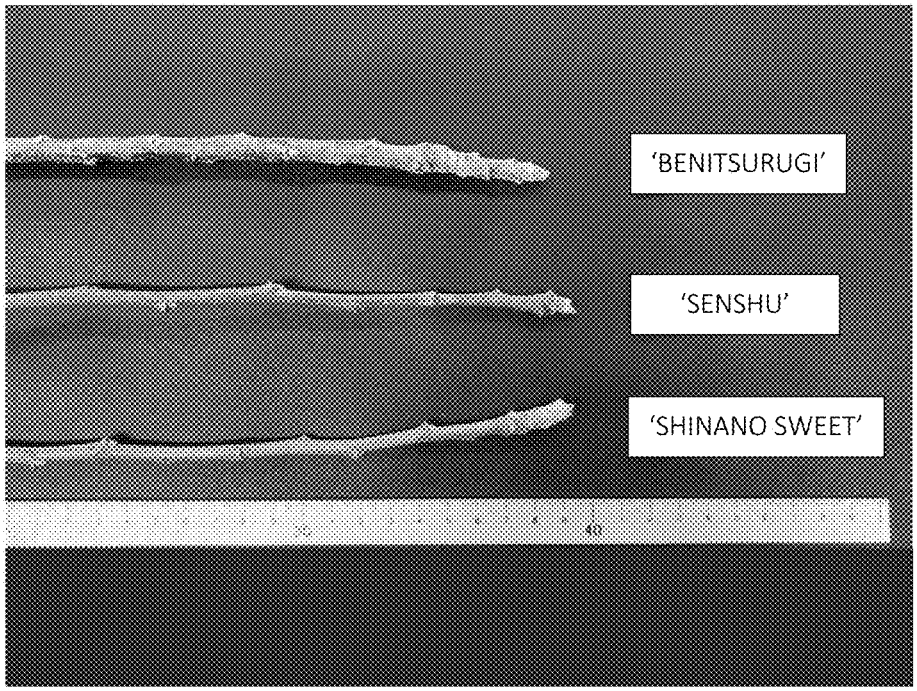
FIG. 7 is a color photograph showing one year old shoot of 'BENITSURUGI' (top), in comparison with 'SENSHU' (middle) and 'SHINANO SWEET' (bottom).
Figure 8:
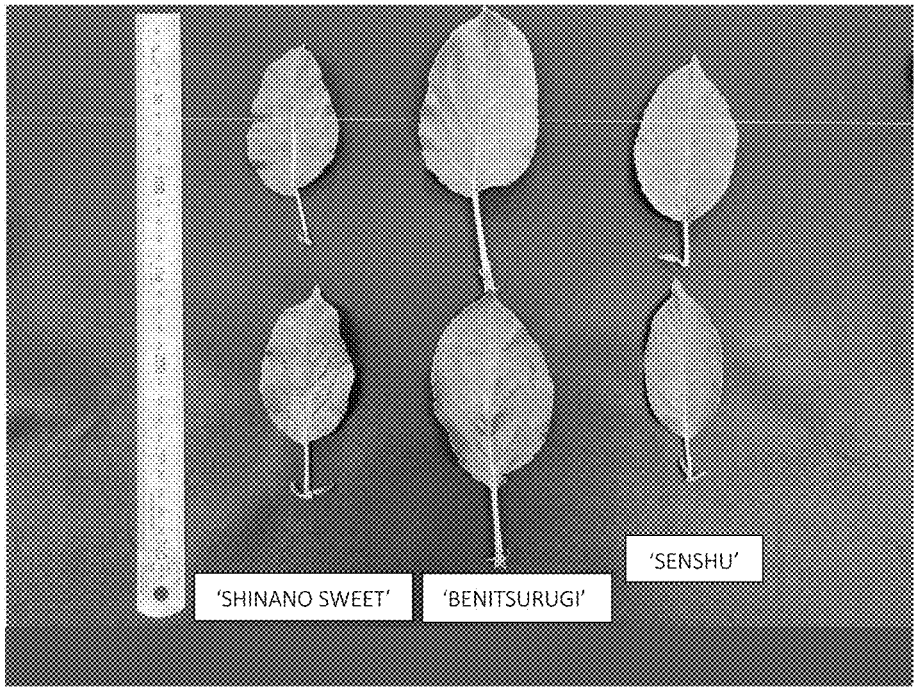
FIG. 8 is a color photograph showing leaves of 'BENITSURUGI' (center), in comparison with 'SHINANO SWEET' (left) and 'SENSHU' (right).
Figure 9A:
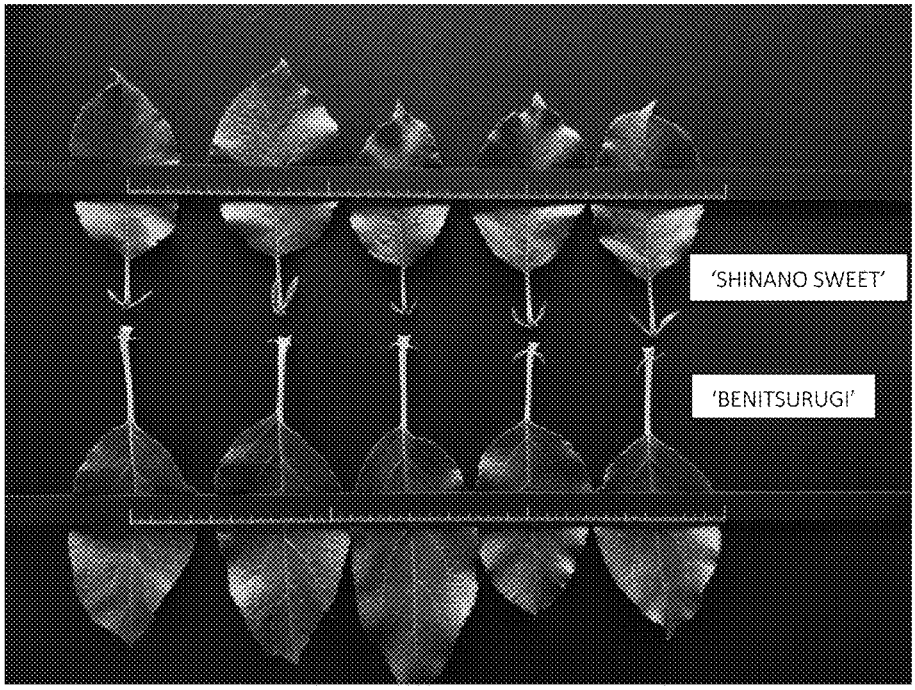
FIG. 9A is a color photograph showing the petiole: extent of anthocyanin coloration from base of 'BENITSURUGI' (bottom), in comparison with 'SHINANO SWEET' (top).
Figure 9B:
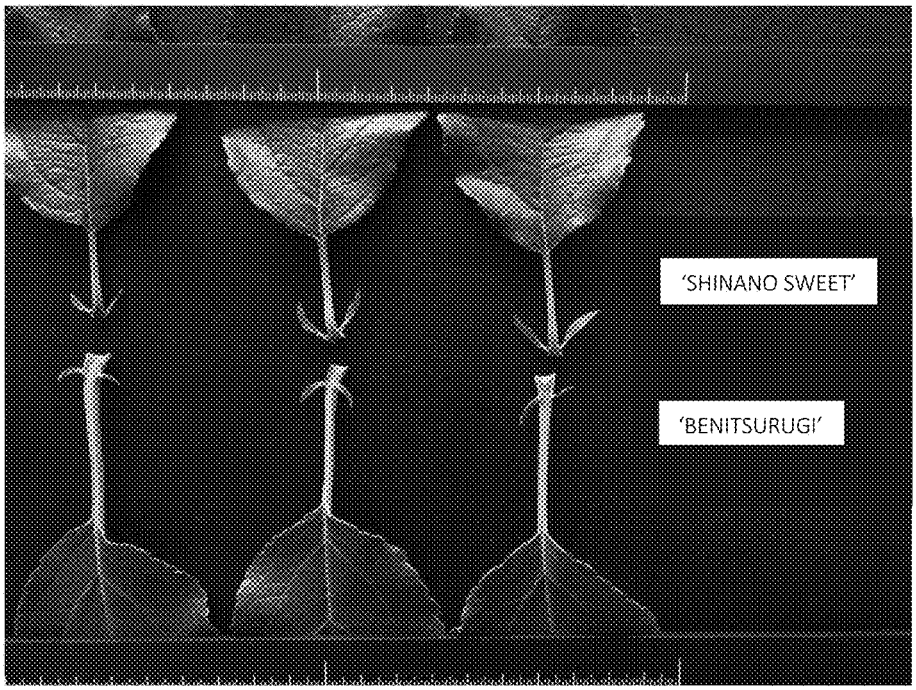
FIG. 9B is a color photograph showing a more detailed view of the petiole: extent of anthocyanin coloration from base of 'BENITSURUGI' (bottom), in comparison with 'SHINANO SWEET' (top).
Figure 10:
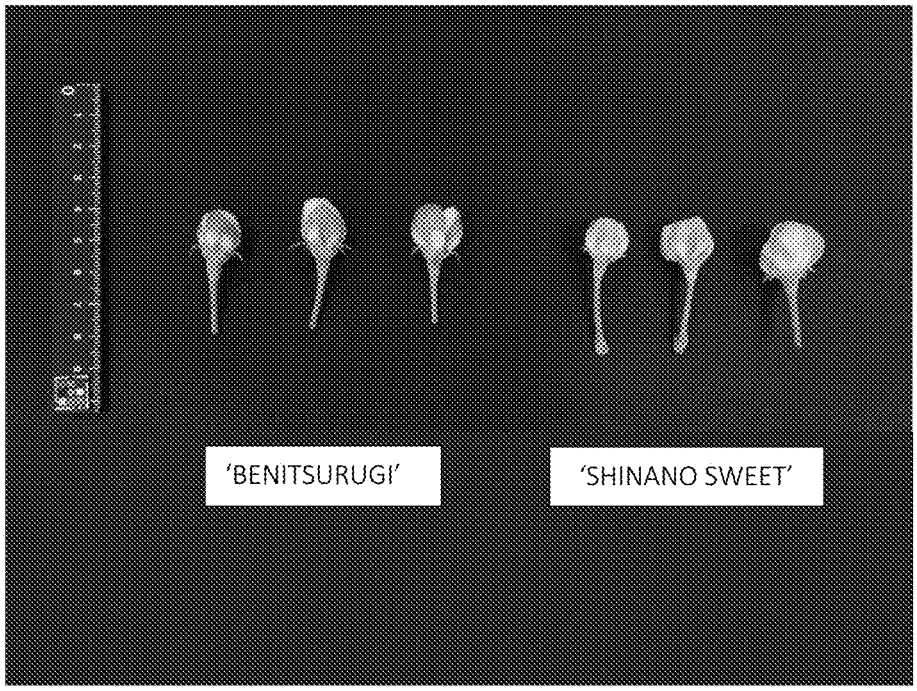
FIG. 10 is a color photograph showing the flower bud of 'BENITSURUGI' (left), in comparison with 'SHINANO SWEET' (right).
Figure 11:
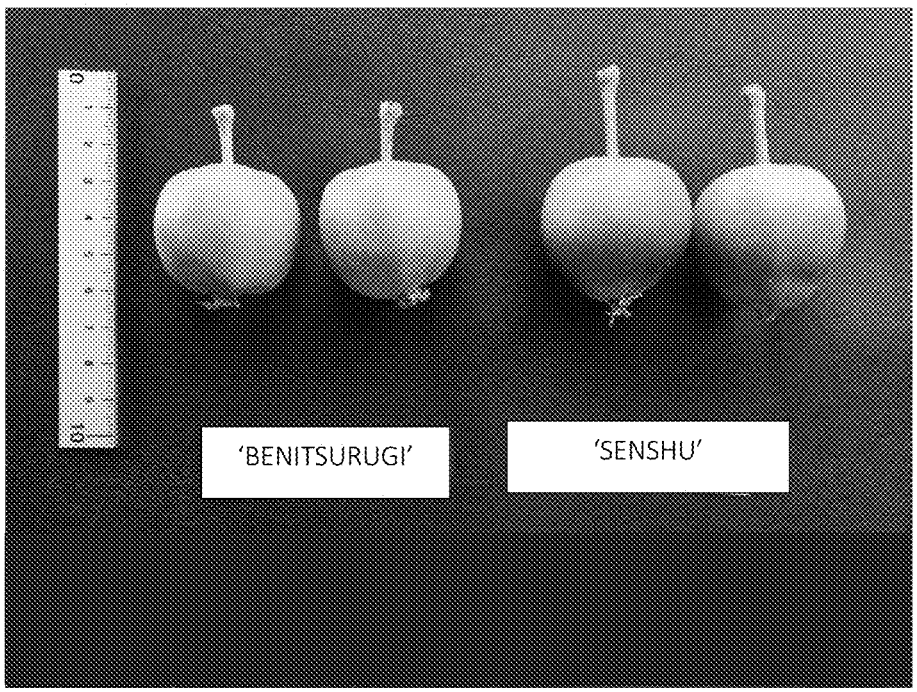
FIG. 11 is a color photograph showing the young fruit of 'BENITSURUGI' (left), in comparison with 'SENSHU' (right).
Figure 12:
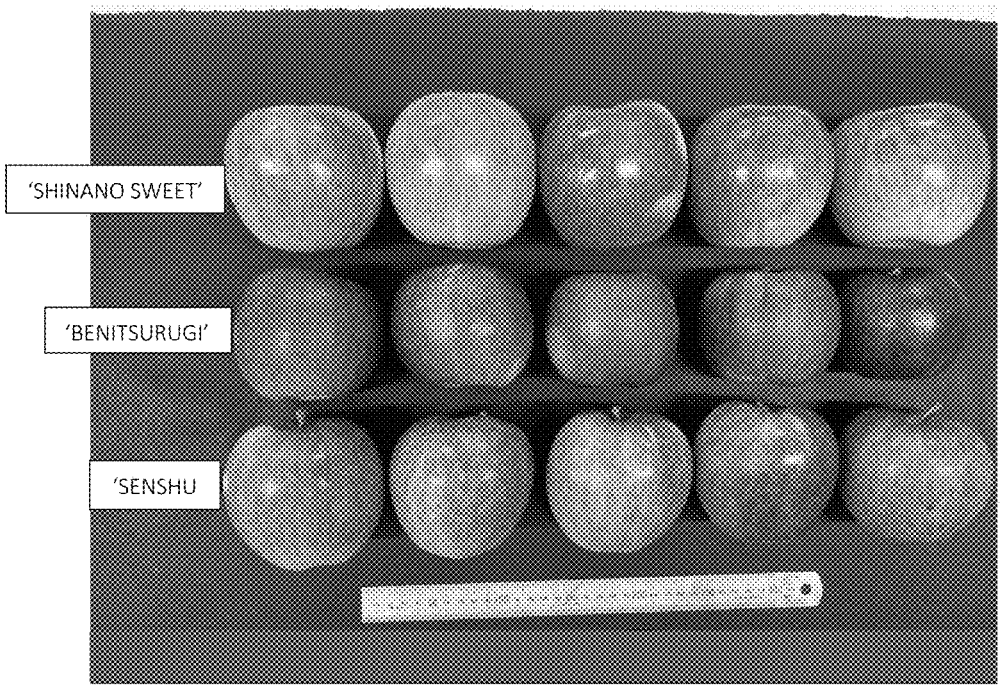
FIG. 12 is a color photograph showing the fruit of 'BENITSURUGI' (center), in comparison with 'SHINANO SWEET' (top) and 'SENSHU' (bottom).
Figure 13:
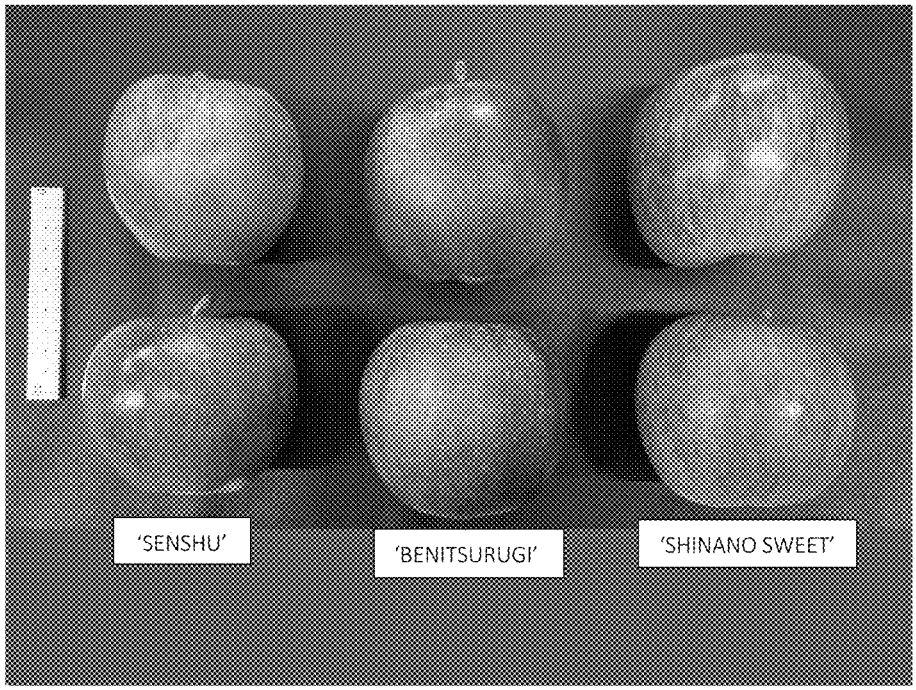
FIG. 13 is a color photograph showing another view of the fruit of 'BENITSURUGI' (center), in comparison with 'SENSHU' (left) and 'SHINANO SWEET' (right).
Figure 14:
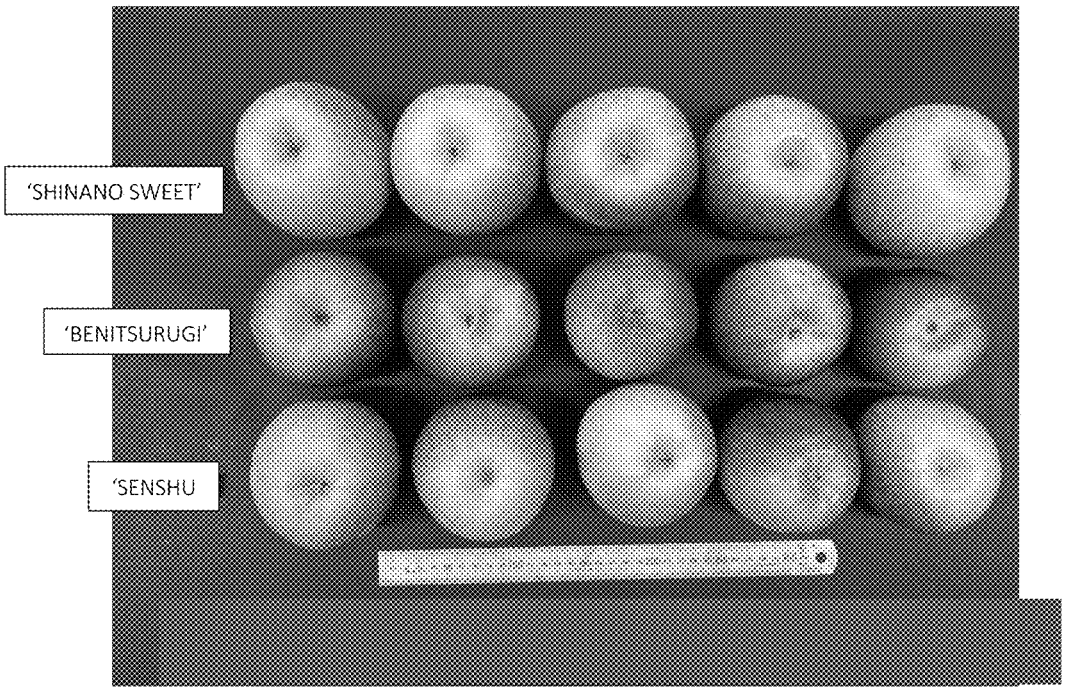
FIG. 14 is a color photograph showing the underside of fruit of 'BENITSURUGI' (middle), in comparison with 'SHINANO SWEET' (top) and 'SENSHU' (bottom).
Figure 15:
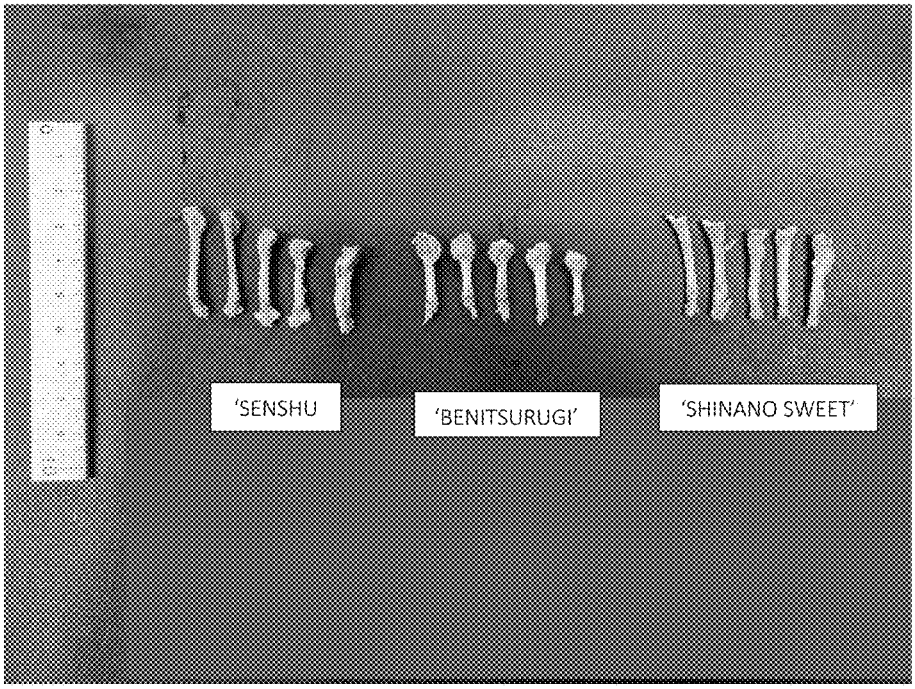
FIG. 15 is a color photograph showing the fruit stalk of 'BENITSURUGI' (center), in comparison with 'SENSHU' (left) and 'SHINANO SWEET' (right).
Figure 16:
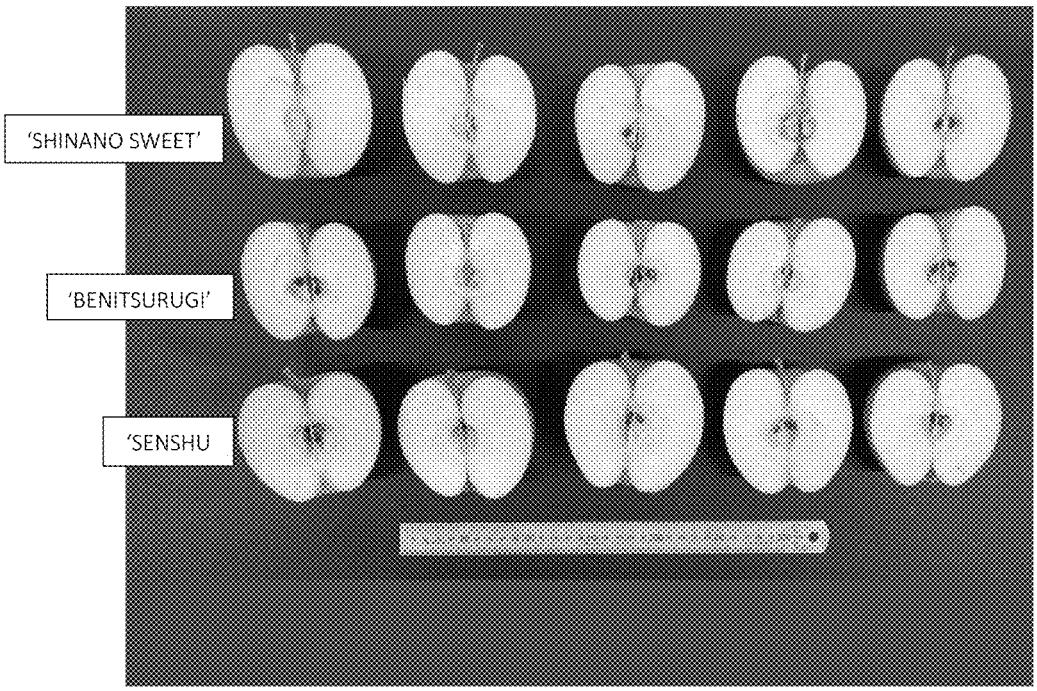
FIG. 16 is a color photograph showing the fruit shape of core of 'BENITSURUGI' (middle), in comparison with 'SHINANO SWEET' (top) and 'SENSHU' (bottom).
Figure 17:
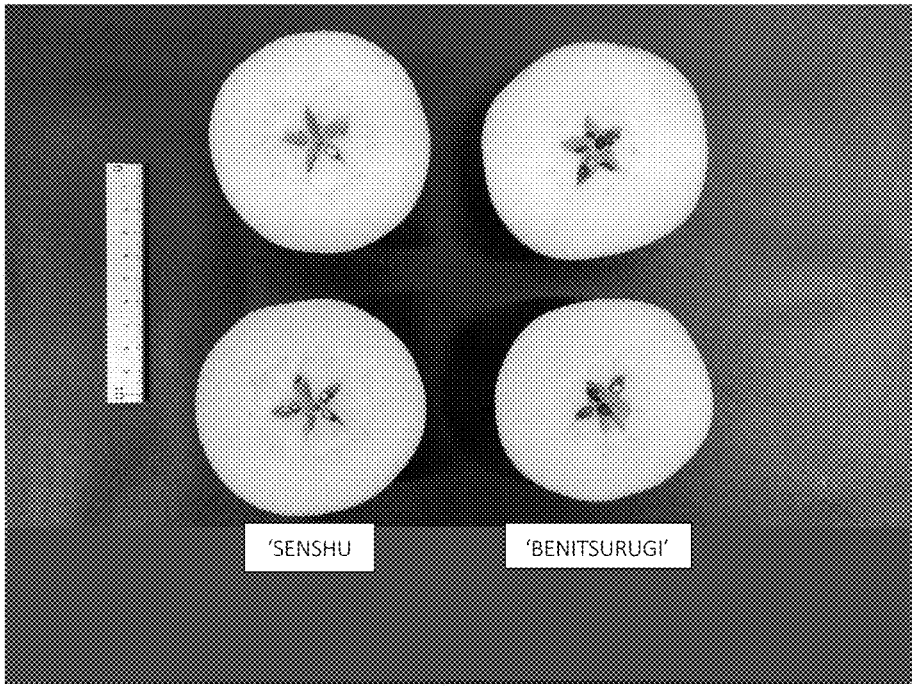
FIG. 17 is a color photograph showing the aperture of locules in transverse section of the fruit of 'BENITSURUGI' (right), in comparison with 'SENSHU' (left).
Figure 18:
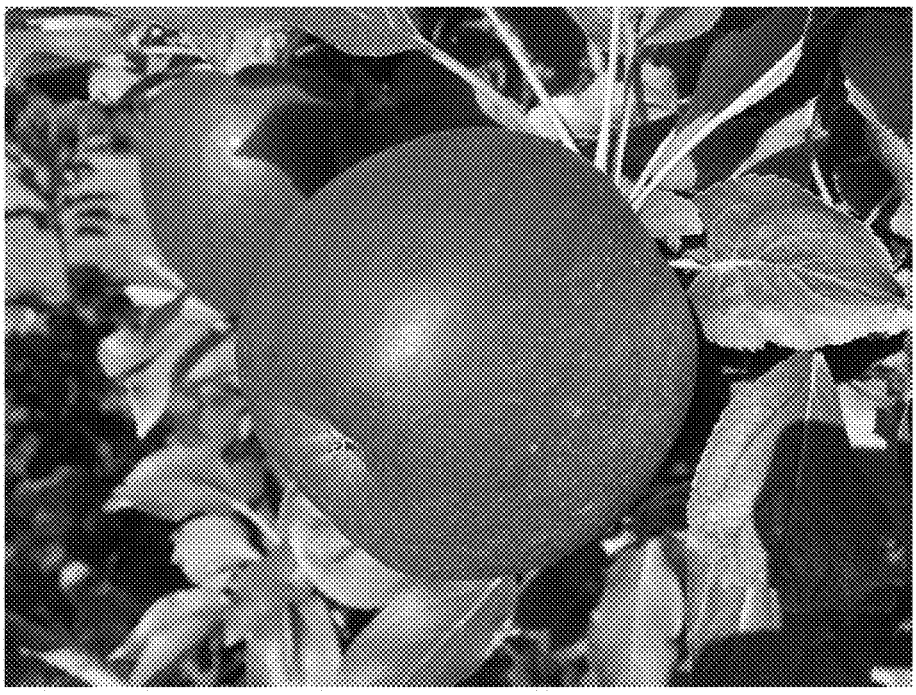
FIG. 18 is a color photograph showing a general view of the fruit of 'BENITSURUGI'.

The dates each photograph was taken are as follows:

FIGS. 1, 18: Oct. 2, 2020,
FIGS. 2, 3: May 11, 2020
FIGS. 4, 5: Oct. 9, 2020
FIGS. 6A, 6B, 6C: Sep. 29, 2022
FIG. 7: Dec. 23, 2022
FIGS. 8, 12, 16: Dec. 15, 2022
FIG. 9A, 9B: Aug. 24, 2020
FIG. 10: May 10, 2021
FIG. 11: Jun. 21, 2021
FIGS. 13, 14, 15, 17: Dec. 1, 2021

Colors are given according to The R.H.S. (Royal Horticultural Society) Colour Chart, Sixth Edition, 2015.

BOTANICAL DESCRIPTION

TABLE 4

| No. | Characteristics | States | Values |
|---|---|---|---|
| 1 | Tree: vigor | medium | |
| 2 | Tree: type | columnar | |
| 3 | Tree: average height | | 3.2 m |

TABLE 4-continued

| No. | Characteristics | States | Values |
|---|---|---|---|
| 4 | Tree: average spread | | 1.2 m |
| 5 | Tree: habit | not applicable | |
| 6 | Tree: type of bearing | on spurs only | |
| 7 | Tree: trunk color | medium brown | 166B |
| 8 | Tree: bark surface texture | smooth-medium | |
| 9 | One-year-old shoot: thickness | thick to very thick | 8.2 mm |
| 10 | One-year-old shoot: length of internode | short | 1.2 cm |
| 11 | One-year-old shoot: color on sunny side | medium brown | 200A (dark brown) |
| 12 | One-year-old shoot: pubescence (on distal half of shoot) | strong | |
| 13 | One-year-old shoot: number of lenticels | many | |
| 14 | Leaf blade: attitude in relation to shoot | outwards | |
| 15 | Leaf blade: length | long | 11.5 cm |
| 16 | Leaf blade: width | medium to broad | 6.6 cm |
| 17 | Leaf blade: ratio length/width | medium to large | 1.7 |
| 18 | Leaf blade: intensity of green color (upper surface) | dark green | 139A |
| 19 | Leaf blade: intensity of green color (lower surface) | light green | 142C |
| 20 | Leaf blade: incisions of margin (upper half) | serrate type 2 (crenate to serrate) | |
| 21 | Leaf blade: pubescence on lower side | medium | |
| 22 | Petiole: length | long | 4.6 cm |
| 23 | Petiole: extent of anthocyanin coloration from base | small | 22.50% |
| 24 | Petiole: color | light green | 145C |
| 25 | Leaf stipule: length | | 11.0 mm |
| 26 | Leaf stipule: width | | 2.5 mm |
| 27 | Leaf stipule: shape | long round | |
| 28 | Leaf stipule: color | medium green | 143B |
| 29 | Flowers: average number per spur | 5 flowers per cluster | |
| 30 | Flower: predominant color at balloon stage | purplish pink | N74C |
| 31 | Flower: diameter with petals pressed into horizontal position | small to medium | 4.8 cm |
| 32 | Flower: arrangement of petals | overlapping | |
| 33 | Flower: position of stigmas relative to anthers | same level | |
| 34 | Young fruit: extent of anthocyanin overcolor | absent or very small to small | 10.70% |
| 35 | Sepal: length | | 8.6 mm |
| 36 | Sepal: width | | 5.0 mm |
| 37 | Sepal: shape | deltoid | |
| 38 | Sepal: surface texture | smooth with medium pubescence | |
| 39 | Sepal: color | light green | 141D |
| 40 | Pedicel: length | | 16.3 mm |
| 41 | Pedicel: width | | 2.1 mm |
| 42 | Pedicel: surface texture | smooth with medium pubescence | |
| 43 | Pedicel: color | medium brown green | 146D |
| 44 | Reproductive organs: number of stamens per flower | | 20 |
| 45 | Reproductive organs: number of styles per flower | | 5 |
| 46 | Reproductive organs: length of stamen | | 8.4 mm |

TABLE 4-continued

| No. | Characteristics | States | Values |
|---|---|---|---|
| 47 | Reproductive organs: length of anther | | 2.7 mm |
| 48 | Reproductive organs: length of style | | 6.2 mm |
| 49 | Reproductive organs: color of filament | white | 155A |
| 50 | Reproductive organs: color of anther | light yellow | 5D |
| 51 | Reproductive organs: color of style | light green | 145B |
| 52 | Reproductive organs: color of stigma | light green | 144D |
| 53 | Reproductive organs: color of ovary | light green | 145B |
| 54 | Seed: number per fruit | | 8.6 |
| 55 | Seed: number per fruit cell | | 1.6 |
| 56 | Seed: length | | 8.3 mm |
| 57 | Seed width | | 4.8 mm |
| 58 | Seed: depth | | 3.3 mm |
| 59 | Seed: shape | obtuse | |
| 60 | Seed: color (with RHS number) | dark brown | 187A |
| 61 | Fruit: size | medium | 311.5 g |
| 62 | Fruit: height | short to medium | 8 cm |
| 63 | Fruit: diameter | medium | 9.1 cm |
| 64 | Fruit: ratio height/diameter | medium | 0.88 |
| 65 | Fruit: general shape | globose | |
| 66 | Fruit: ribbing | absent or weak | |
| 67 | Fruit: crowning at calyx end | absent or weak | |
| 68 | Fruit: size of eye | very small to small | |
| 69 | Fruit: length of sepal | short to medium | |
| 70 | Fruit: bloom of skin | absent or weak | |
| 71 | Fruit: greasiness of skin | absent or weak | |
| 72 | Fruit: surface texture of skin | smooth | |
| 73 | Fruit: ground color | yellow green | 150C (yellow green) |
| 74 | Fruit: relative area of over color | large | 87.7% |
| 75 | Fruit: hue of over color-with bloom removed | red | 187B (dark purple red) |
| 76 | Fruit: intensity of over color | dark | |
| 77 | Fruit: pattern of over color | solid flush with weakly defined stripes | |
| 78 | Fruit: width of stripes | narrow to medium | |
| 79 | Fruit: intensity of stripes | weak to medium | |
| 80 | Fruit: area of russet around stalk attachment | absent or small | |
| 81 | Fruit: area of russet on cheeks | absent or small | |
| 82 | Fruit: area of russet around eye basin | absent or small | |
| 83 | Fruit: number of lenticels | medium | |
| 84 | Fruit: size of lenticels | small to medium | |

TABLE 4-continued

| No. | Characteristics | States | Values |
|---|---|---|---|
| 85 | Fruit: scarfskin | very small to small | |
| 86 | Fruit: length of stalk | short to medium | 1.8 cm |
| 87 | Fruit: thickness of stalk | thin to medium | 3.1 mm |
| 88 | Fruit: depth of stalk cavity | shallow medium | 2.2 cm |
| 89 | Fruit: width of stalk cavity | narrow medium | 4 cm |
| 90 | Fruit: depth of eye basin | medium | 1.2 cm |
| 91 | Fruit: width of eye basin | medium | 3.4 cm |
| 92 | Fruit: firmness of flesh | medium | 15 lbs |
| 93 | Fruit: color of flesh | cream | 8D (light yellow) |
| 94 | Fruit: sweetness of flesh | medium | 13.5 % |
| 95 | Fruit: acidity of flesh | low | 0.36 g/100 ml |
| 96 | Fruit: water-core of flesh | absent or very slight | |
| 97 | Fruit: shape of core | flat round | |
| 98 | Fruit: aperture of locules (in transverse section) | fully open | |
| 99 | Pollination requirements | flowers are self-incompatible, S genotype is S3S5 and requires pollination by another S genotype diploid apple | |
| 100 | Time of beginning of flowering | early to medium | May 9 |
| 101 | Time of harvest | medium | October 2 |
| 102 | Shipping quality | moderate | |
| 103 | Storage life | 6-11 days at room temperature, 1 month at refrigerated temperature | |
| 104 | Market use | fresh, juice, multiple use | |
| 105 | Productivity (weight/plant) | | 22.5 kg/tree (average for 7-8 year-old tree) |
| 106 | Resistance to: Alternaria blotch | strong | |

Other features of the plant are as follows:

Disease resistance: Resistance to *Alternaria* blotch (*Alternaria alternata*) was observed. The new variety has the same susceptibility to Blotch (*Diplocarpon mali*), Powdery mildew (*Podosphaera leucotricha*) and Scab (*Venturia inaequalis*) as existing cultivars.

I/we claim:

1. A new and distinct variety of apple tree named 'BENITSURUGI', substantially as described and illustrated herein.

* * * * *